United States Patent
Tanbun-Ek et al.

(10) Patent No.: US 6,597,718 B2
(45) Date of Patent: Jul. 22, 2003

(54) ELECTROABSORPTION-MODULATED FABRY PEROT LASER

(75) Inventors: Tawee Tanbun-Ek, Califon, NJ (US); Won-Tien Tsang, Holmdel, NJ (US); Liang David Tzeng, Belle Mead, NJ (US)

(73) Assignee: Multiplex, Inc., South Plainfield, NJ (US)

( * ) Notice: Subject to any disclaimer, the term of this patent is extended or adjusted under 35 U.S.C. 154(b) by 0 days.

(21) Appl. No.: 09/907,246

(22) Filed: Jul. 17, 2001

(65) Prior Publication Data

US 2002/0009114 A1 Jan. 24, 2002

Related U.S. Application Data

(60) Provisional application No. 60/218,918, filed on Jul. 18, 2000.

(51) Int. Cl.$^7$ ............................................... H01S 5/00
(52) U.S. Cl. ......................... 372/50; 372/50; 372/45; 437/127
(58) Field of Search ............................................ 372/50

(56) References Cited

U.S. PATENT DOCUMENTS

| | | | | |
|---|---|---|---|---|
| 3,952,404 A | * | 4/1976 | Matunami | 257/735 |
| 4,961,198 A | * | 10/1990 | Ishino et al. | 257/14 |
| 5,165,105 A | * | 11/1992 | Haase et al. | 385/131 |
| 5,543,353 A | * | 8/1996 | Suzuki et al. | 438/31 |
| 5,548,607 A | * | 8/1996 | Tsang | 372/102 |
| 5,680,411 A | * | 10/1997 | Ramdane et al. | 372/102 |
| 5,745,511 A | * | 4/1998 | Leger | 372/102 |
| 5,787,106 A | * | 7/1998 | Tabuchi et al. | 372/46 |
| 5,987,046 A | * | 11/1999 | Kobayashi et al. | 372/45 |
| 5,991,322 A | * | 11/1999 | Takiguchi et al. | 372/50 |
| 6,108,362 A | * | 8/2000 | Adams et al. | 372/50 |
| 6,150,667 A | * | 11/2000 | Ishizaka et al. | 257/184 |

OTHER PUBLICATIONS

T. Tanbun–Ek et al., "10 Gbit/s Penalty–Free Tranmission Over 48 km Using 1.3–$\mu$m Wavelength Electroabsorption Modulated Lasers (EML) for Metro–Loop Transmission Link", Optical Fiber Communications Technical Digest, San Jose, CA, pp. 207, paper ThB4, (1996).

M. Aoki et al., "High–Extinction–Ratio MQW Electroabsorption–Modulator Integrated DFB Laser Fabricated by In–Plane Bandgap Energy Control Technique," IEEE Photonics Technology Letters, vol. 4 pp. 580, (1992).

T. Tanbun–Ek et al., "Integrated DFB–DBR Laser Modulator Grown by Selective Area Metalorganic Vapor Phase Epitaxy Growth Technique," in $7^{th}$ International Conference on Metalorganic Vapor Phase Epitaxy, Yokohama, Japan, (1994).

J.E. Johnson et al., "Low–Chirp Integrated EA–Modulator/DFB Laser Grown by Selective–Area MOVPE," in $14^{th}$ IEEE International Semiconductor Laser Conference, Maui, Paper M4.7 (1994).

J.E. Johnson et al., "Integrated Electroabsorption Modulators for WDM Systems," in LEOS '95 Conference Proceedings, San Francisco, CA, paper 105.2 (1995).

(List continued on next page.)

Primary Examiner—Paul Ip
Assistant Examiner—Tuan Nguyen
(74) Attorney, Agent, or Firm—Testa, Hurwitz & Thibeault, LLP

(57) ABSTRACT

An electroabsorption modulated laser (EML) is formed to include a Fabry-Perot lasing section, in place of the conventional DFB lasing section. When operated at a wavelength of 1310 nm, the wider spectral bandwidth of the FP device (containing several longitudinal modes) is of no concern, since 1310 nm is the zero dispersion wavelength of most conventional transmission fibers. A selective area growth process is used to simultaneously form the MQW active regions of both the FP and EA sections of the EML device, and an isolation trench may be formed between the sections to reduce the effects of electrical crosstalk.

17 Claims, 4 Drawing Sheets

OTHER PUBLICATIONS

P.A. Morton et al., "High–speed Integrated DFB/Electroabsorption Modulated Lasers," in Conference on Lasers and Electo–Optics 1996 Technical digest, Anaheim, CA, paper CWL1. (1996), (ABSTRACT ONLY).

Y. K. Park et al., "Dispersion–Penalty–Free Transmission Over 130–km Standard Fiber Using a 1.55–$\mu$m, 10–Gb/s Integrated EA/DFB Laser with Low–Extinction Ratio and Negative Chirp," IEEE Photonics Technology Lett., vol. 8, No. 9, pp. 1255–1257.

* cited by examiner

ELECTROABSORPTION-MODULATED FABRY PEROT LASER

CROSS REFERENCE TO RELATED APPLICATION

This application claims the benefit of Provisional Application No. 60/218,918, filed Jul. 18, 2000.

TECHNICAL FIELD

The present invention relates to an electroabsorption-modulated laser (EML) device and, more particularly, to an EML operating at a wavelength of 1310 nm by using a Fabry-Perot (FP) structure as its lasing section.

TECHNICAL FIELD

Optical transmitters, transceivers, and transponders utilizing electroabsorption modulated lasers (EMLs) at bit rates of up to 10 Gb/sec are of increasing interest, particularly when compared to the performance of directly modulated lasers. The zero dispersion property of conventional optical fiber at wavelengths close to 1300 nm makes the option of using a 1300 nm EML even more attractive than a 1550 nm EML, due to the non-existent dispersion penalty at the latter wavelength. Further, the modulation speed of an EML device is limited only by the RC time constant in the modulator section of the device. EML devices with a small enough device capacitance enable system designers to realize transmitters and transponders with speeds over 10 Gb/sec without the complication of the relaxation resonance frequency effects incurred in the directly modulated distributed feedback (DFB) or Fabry Perot (FP) lasers. In additional EML devices can be designed with a very high extinction ratio and system sensitivity penalties associated with this parameter can be virtually eliminated.

At the present invention, 1500 nm EMLs are being deployed in high speed (e.g., 2.5 Gb/sec and 10 Gb/sec) fiber optic networks. One exemplary EML arrangement is discussed in the article The advantage of these devices, as compared to conventional directly modulated DFBs, is that EML lasers exhibit highly superior eye diagrams, with less pulse distortion/ringing minimal chirp characteristics, high extinction ratio, and simplified driver circuitry. However, these advantages are obtained at the expense of a more complicated chip design, requiring multiple epitaxial regrowth steps, and additional wafer processing procedures to obtain electrical isolation between the electroabsorption modulator and laser sections of the device. Moreover, EML devices require tightly confined matching of the optical characteristics between the DFB grating, the active material gain characteristics, and the modulator material absorption characteristics. The combination of these factors can result in low yields and high costs, particularly when manufactured in high volume. Therefore, any new innovations which can relax any of the above requirements of the EML design can have considerable commercial impact and lead to competitive advantages.

At the same time, there is a rapid increase in the deployment of fiber-optic-based equipment which utilizes transponder, transceiver and transmitter modules operating at 10 Gbit/sec and at wavelengths near the 1310 nm dispersion minimum of the optical fiber. Currently, directly modulated 1310 nm DFB or FP lasers are utilized in these types of applications. However, directly modulated DFB or FP lasers exhibit severe limitations due to relaxation oscillation effects and the difficulties of modulating the drive current at 10 Gb/sec. The advantages of utilizing an EML laser operating at 1310 nm are significant, for the same reasons outlined in the previous paragraph. Some development work has moved forward regarding a 1310 nm EML, as discussed in the article "10 Gbit/s penalty-free transmission over 48 km using 1.3-$\mu$m wavelength electroabsorption modulated lasers (EML) for metro-loop transmission link", by T. Tanbun-Ek et al, appearing in OFC Proceedings, San Jose Calif., 1996, at p.207. However, the research discussed in this and other papers presumes the use of a DFB section as the lasing device, requiring a complicated fabrication sequence, which is subject to low yields and high costs.

Thus, a need remains in the art for an EML device that is less costly and easier to manufacture than DFB-EML devices, yet is capable of operating at a wavelength of approximately 1310 nm.

SUMMARY OF THE INVENTION

The need remaining in the prior art is addressed by the present invention, which relates to an electroabsorption-modulated laser (EML) device and, more particularly, to an EML operating at a wavelength of 1310 nm by using a Fabry-Perot (FP) structure as its lasing section.

In accordance with the present invention, an FP laser and electroabsorption (EA) modulator are simultaneously formed on a common InP substrate, using (for example) a selective area growth (SAG) process. A trench is formed between the top conducting layers of the two sections to provide for electrical isolation between the FP laser and the EA modulator.

It is an advantage of the present invention that even though an FP laser exhibits a wider spectral bandwidth than the DFB laser conventionally used in an EML structure, the bandwidth is not a concern when operating at 1310 nm, the zero dispersion wavelength of the transmission fiber.

Other and further advantages of the present invention will become apparent during the course of the following discussion and by reference to the accompanying drawings.

BRIEF DESCRIPTION OF THE DRAWINGS

Referring now to the drawings, where like numerals reference like parts in several views.

DETAILED DESCRIPTION

Figure 1:
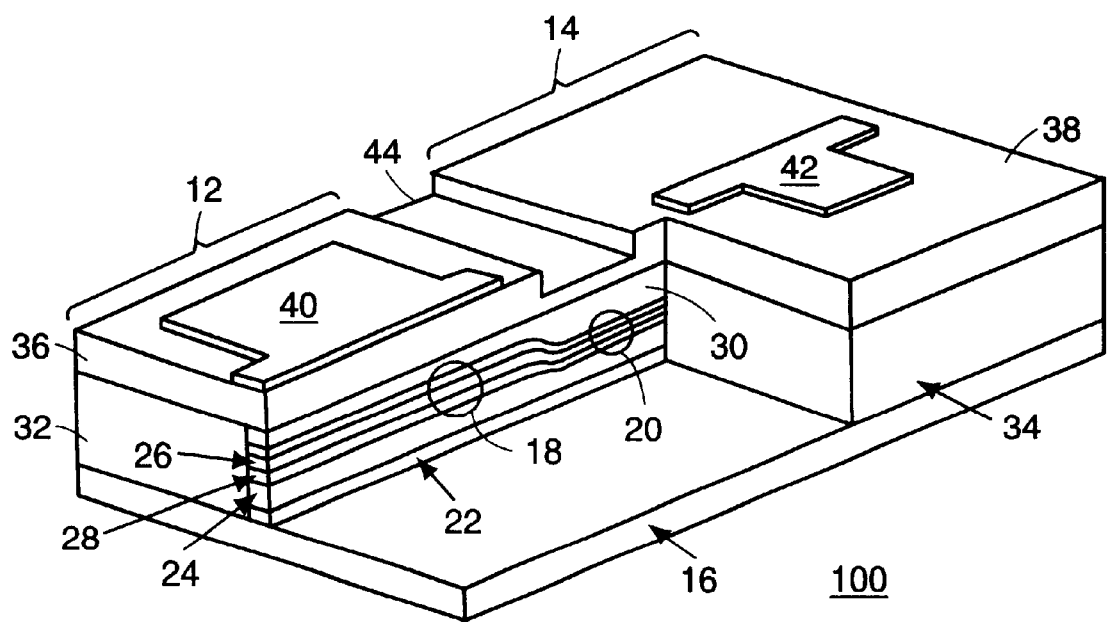
FIG. 1 contains an isometric view of a Fabry-Perot electroabsorption modulated laser (FP-EML) formed in accordance with the present invention.
Figure 2:
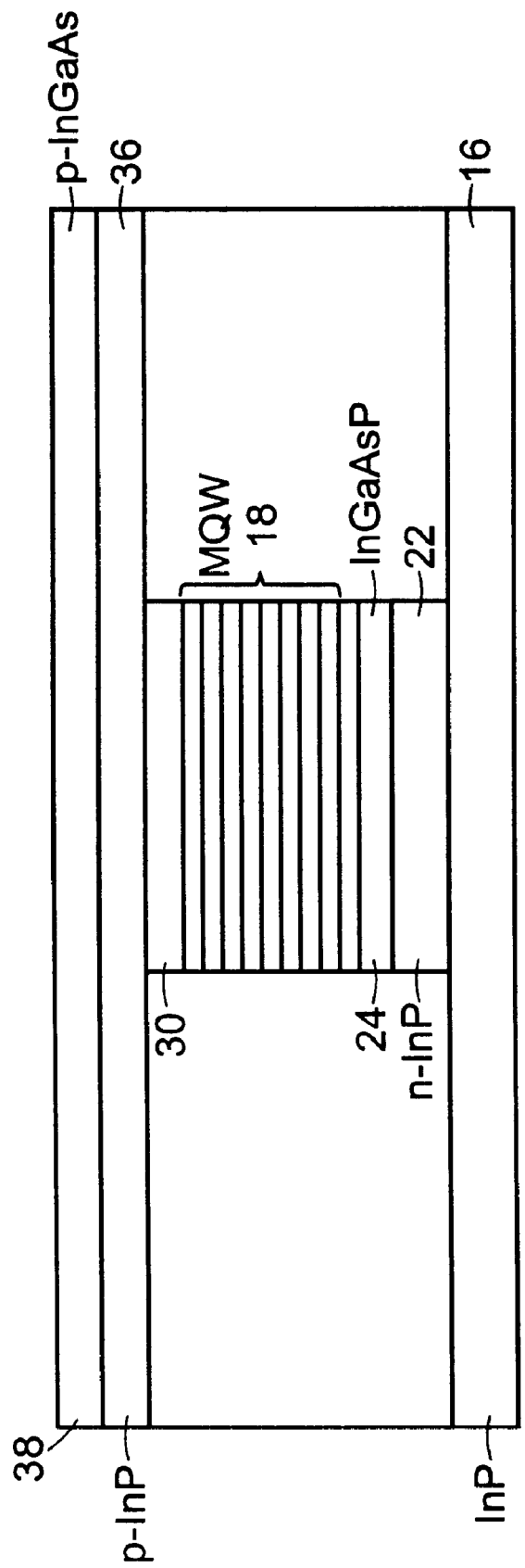
FIG. 2 is an end view of the structure of FIG. 1.

A cut-away isometric view of a Fabry-Perot electroabsorption modulated laser (FP-EML) 10 formed in accordance with the present invention is illustrated in FIG. 1, comprising an FP laser section 12 and EA modulator section 14. FIG. 2 contains an end view of FP-EML 10, illustrating the laser end facet of the device. As in the case of all electroabsorption modulated devices, FP laser 12 section is operated in CW mode and EA modulator section 14 is subjected to an input electrical modulation signal to cause the optical output modulation in laser section 12. Both FP laser 12 and EA modulator 14 are formed on a common InP substrate 16, where FP laser 10 comprises a multiple quantum well (MQW) action region 18 which transitions to become a MQW action region 20 in EA modulator 18. As will be described in detail below in association with FIGS.

3–5, a selective area growth (SAG) technique may be used to form this MQW structure and insure that active region 18 in laser 12 is emissive (relatively thick MQW layers), while active region 20 in EA modulator 14 is absorptive (relatively thin MQW layers). The transition between the MQW layer thickness is evident in area 22 of the cut-away view of FIG. 1.

Referring to both FIGS. 1 and 2, FP-EML 10 comprises a first n-InP buffer layer 22, covered by a separate confinement heterostructure (SCH) InGaAsP layer 24. Preferably, first n-InP buffer layer 22 comprises a thickness on the order of 100 nm and SCH layer 24 comprises a thickness of approximately 70 nm and exhibits a band gap wavelength of 1.15 micron. MQW action regions 18 and 20 are formed over SCH layer 24, preferably using the SAG process. In a preferred embodiment, between 7 and 9 pairs of "barrier" 26 and "well" 28 layers are formed, where for FP laser section 12, the layers are grown in a manner to provide lasing at the desired wavelength. For some embodiments, a device which lases in the wavelength range of 1260–1600 nm is desirable. Other arrangements require a device which lases in the wavelength range of 700–1000 nm. Some conventional EML devices have exhibited excellent characteristics at a wavelength of approximately 1550. An advantage of the FP-EML structure of the present invention is that the FP device can be formed to exhibit a wavelength of 1310 nm, which cannot be achieved using a conventional DFB device in the EML structure. In general, the use of a SAG process to form the MQW active region allows for the FP-EML device of the present invention to be tailored to emit at a wavelength chosen by the designer for a specific system implementation.

Referring back to FIG. 1, a second InGaAsP SCH layer 30 is formed over MWQ active regions 18, 20. Current blocking in the device is provided by Fe-doped InP barriers 32 and 34, formed on either side of the active waveguiding region of FP-EML 10.

A p-InP cladding layer 36 is then formed on the top surface of device 10, followed by a p-InGaAs contact layer 38. A first electrical contact pad 40, associated with FP laser 12, is deposited on contact layer 38 over the location of active region 18. A second electrical contact pad 42, associated with EA modulator 14, is deposited on contact layer 38 over the location of active region 20. In a preferred embodiment, first and second electrical contact pads comprise a tri-layer Ti—Pt—Au structure.

In accordance with the properties of the FP-EML device of the present invention, an isolation trench 44 is formed between FP laser section 12 and EA modulator 14, as shown in FIG. 1. In a preferred embodiment, trench 44 comprises a depth of approximately 0.7 microns (into p-InP cladding layer 36) and a width of approximately 20 microns. Trench 44 may be formed using conventional reactive ion etching (RIE) techniques and is used to reduce electrical crosstalk between FP laser section 12 and EA modulator section 14.

Figure 3:
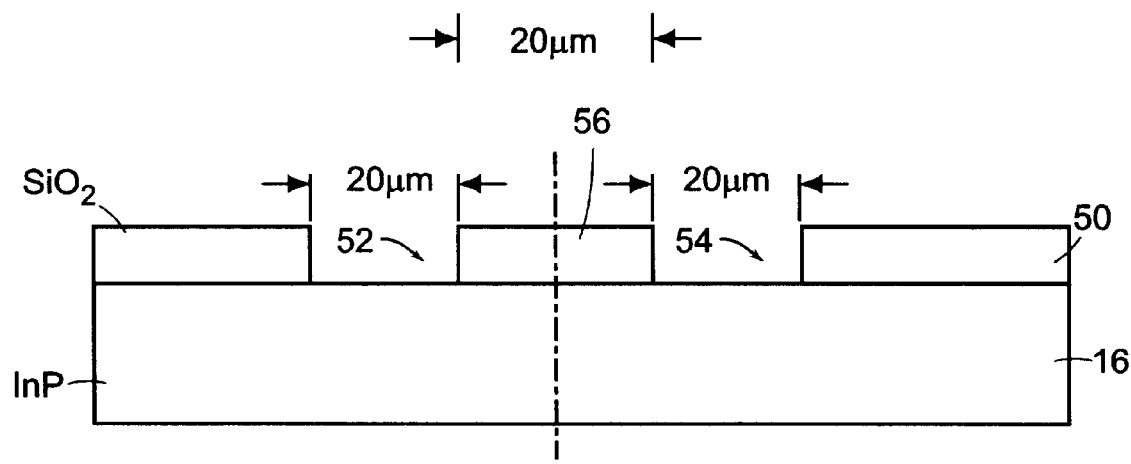
FIGS. 3–7 illustrate an exemplary set of process steps used to form the FP-EML of the present invention.
Figure 4:
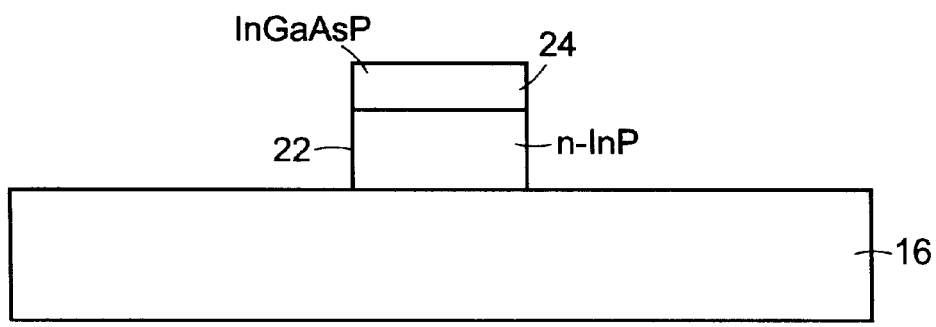
Figures 5, 6:
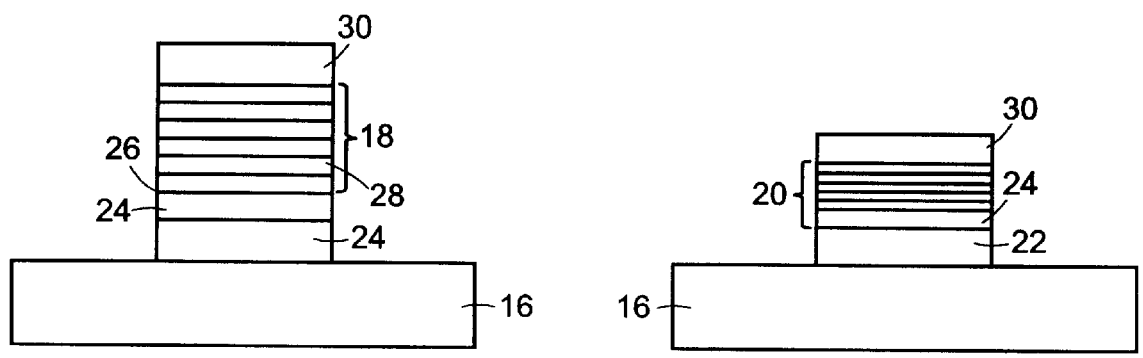

FIGS. 3–7 describe an exemplary set of processing steps for fabricating an FP-EML device in accordance with the present invention. Referring to FIG. 3, InP substrate 16 is first covered with a relatively thick (e.g., 300 nm) layer 50 of $SiO_2$, which may be deposited using a convention PECVD technique. Layer 50 is then masked and etched to form a pair of suitable width stripes 52 and 54 (for example, 20 μm in width), separated by a 20 μm wide barrier 56. A separation FP-EML device is formed, in accordance with the present invention along each stripe 52 and 54, with barrier 56 used maintain separation between the devices. Once fabrication is completed, the structure is cleaved along the dotted line shown through barrier 56 to separate the devices. It is to be understood that the use of 20 μm as the width for both the stripes and the barrier is a matter of design choice, and has been found to provide the necessary transverse guiding of the output from FP laser section 12. FIGS. 4–7 depict the formation of active regions 18 and 22, starting with the deposit of n-InP buffer layer 22 using an MOCVD process. For the remainder of the discussion, the fabrication steps will illustrate the formation of only a single device, not a pair of devices as shown in FIG. 3. As mentioned above, buffer layer 22 may be formed to comprise a thickness of approximately 100 nm. While remaining in the MOCVD reactor, InGaAsP SCH layer 24 is next deposited, to a thickness of approximately 70 nm. A selective area growth (SAG) process in then initiated (still in the MOCVD reactor), to form the MQW structure active regions 18 and 20 of FP laser section 12 and EA modulator section 14, respectively. FIG. 5 illustrates the formation of active region 18 of FP laser section 12 and FIG. 6 illustrates the formation of action region 20 of EA modulator section 14. As is well-known in the art, a "multiple quantum well" structure comprises alternating layers having a relatively small energy gap ("well layers", i.e., layer 28) and a relatively large energy gap ("barrier" layers, i.e., layer 26). In accordance with the present invention, layers 26 and 28 in FP active region 18 are thicker than in EA active region 20. Only this difference in layer thickness makes it possible to operate section 12 as an active laser and section 14 as an EA modulator. Using the SAG process, surface masking processes are used to impede the growth of each of the barrier and well layers in EA modulator section 14 after a predetermined period of time, allow the barrier and well layers in FP laser section 12 to be relatively thicker. The result is as shown in FIGS. 5 and 6 (where the illustrated difference in the MQW structures is exaggerated for the sake of clarity). Subsequent to the SAG process of forming the MQW structure, an upper SCH p-InP layer 30 is formed to cover active regions 18,20, using the same MOCVD process.

Figure 7:
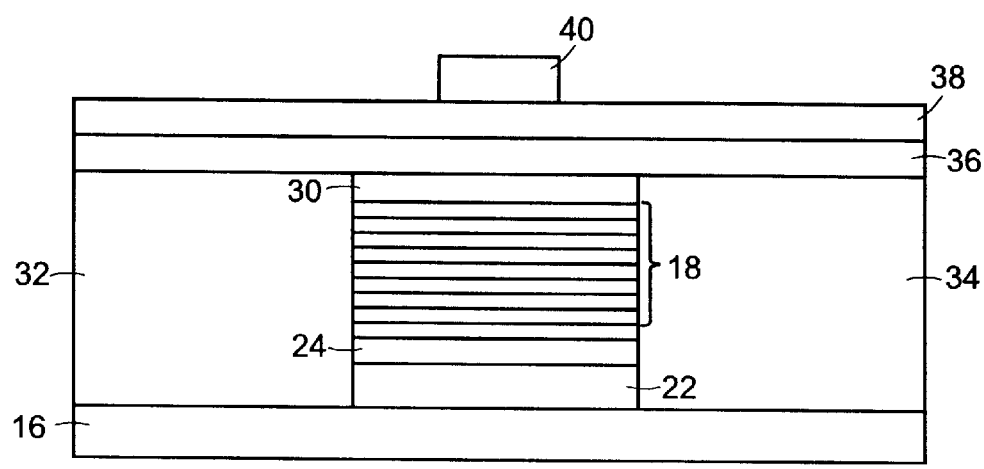

Once the active areas of FP laser section 12 and EA modulator 14 are completed, an epitaxial growth process is performed, using Fe-doped InP, to form current blocking regions 32 and 34 on either side of active regions 18,20, as shown in FIG. 7. The use of Fe-doped InP will impede the spread of the current beyond the central channel region and will also control the transverse mode of the wave propagating through the active region of the device structure. P-InP cladding layer 36 and p-InGaAs contact layer 38 are then grown, in blanket form, to complete the structure. Once these layers are in place, trench 44 (see FIG. 1) may be formed using an RIE process, and contacts 40, 42 deposited at the proper locations on the surface of contact layer 38.

If formed in pairs, the final structure is cleaved along the dotted line shown in FIG. 3. The prior high reflectivity (e.g., 99%) (HR) and anti-reflection (e.g., 10%) (AR) coatings 46, 48 are then formed on the facets of FP laser device 12 and EA modulator device 14, respectively.

What is claimed is:

1. An electroabsorption modulated laser comprising:
   an InP substrate;
   a Fabry-Perot (FP) laser device section comprising a first cladding layer deposited on said InP substrate, a first multiple quantum well (MQW) active region deposited on said first cladding layer and comprising a plurality of barrier layers and a plurality of well layers, a second cladding layer deposited on said first MQW active region, and an electrical contact layer deposited on said second cladding layer, wherein a first electrical contact pad is in electrical communication with said second cladding layer;

an electroabsorption (EA) modulator section comprising said first cladding layer deposited on said InP substrate, a second MQW active region deposited on said first cladding layer and comprising a plurality of barrier layers and a plurality of well layers, said second cladding layer deposited on said second MQW active region, and said electrical contact layer deposited on said second cladding layer, wherein a second electrical contact pad is in electrical communication with said second cladding layer;

a FP laser endface; and an EA modulator endface;

wherein said first MQW active region is optically coupled to said second MQW active region;

wherein said FP laser endface comprises a first reflective coating and said BA modulator endface comprises a first anti-reflective coating;

wherein said first reflective coating and said first anti-reflective coating form a Fabry-Perot cavity; and wherein each of said barrier layers and said well layers of said first MQW region are thicker than each of said barrier layers and said well layers of said second MQW active region, respectively.

2. An electroabsorption modulated laser as defined in claim 1, wherein said laser further comprises an isolation trench disposed through a predetermined thickness of said contact layer and said cladding layer in an area between said Fabry-Perot laser device section and said electroabsorption modulator section.

3. An electroabsorption modulated laser as defined in claim 2 wherein the isolation trench comprises a width of approximately 20 $\mu$m and a depth of approximately 0.7 $\mu$m.

4. An electroabsorption modulated laser as defined in claim 1, wherein said first cladding layer comprises a first layer of n-lnP covered by a first separate confinement heterostructure (SCH) layer of InGaAsP.

5. An electroabsorption modulated laser as defined in claim 1, wherein said second cladding layer comprises a second separate confinement heterostructure (SCH) layer of InGaAsP covered by a first layer of p-InP.

6. An electroabsorption modulated laser as defined in claim 1 wherein the first MQW active region comprises alternating barrier and well layers having thicknesses sufficient to provide lasing in the region of 1260–1600 nm.

7. An electroabsorption modulated laser as defined in claim 1 wherein the first MQW active region comprises alternating barrier and well layers having thicknesses sufficient to provide lasing in the region of 700–1000 nm.

8. An electroabsorption modulated laser as defined in claim 1 wherein the first MQW active region comprises alternating barrier and well layers having thicknesses sufficient to provide lasing at a wavelength of approximately 1550 nm.

9. An electroabsorption modulated laser as defined in claim 1 wherein the first MQW active region comprises alternating barrier and well layers having thicknesses sufficient to provide laser at a wavelength of approximately 1310 nm.

10. An electroabsorption modulated laser as defined in claim 1 wherein the first and second electrical contact pads comprise a Ti—Pt—Au structure.

11. A method for making a Fabry-Perot electroabsorption modulated laser, the method comprising the steps of:

a) providing an InP substrate including a top major surface;

b) covering said InP substrate top major surface with a masking layer;

c) etching a stripe in said masking layer to define the region wherein said laser will be formed;

d) depositing a first cladding layer comprising n-InP in the exposed stripe;

e) depositing a first separate confinement heterostructure (SCH) layer of InGaAsP to cover said first cladding layer;

f) forming a first MQW structure active region for a Fabry-Perot (FP) laser and a second MQW structure active region for an electroabsorption (EA) modulator on said first SCH layer, wherein said first MQW active region is optically coupled to said second MQW active region and said FP laser region exhibits thicker barrier and well layers than said EA modulator barrier and well layers;

g) depositing a second SCH layer of InGaAsP to cover said MQW structures;

h) removing the remaining mask layer and growing Fe-doped InP current blocking regions on the exposed substrate surface to be coextensive with said second SCH InGaAsP layer;

i) depositing a second cladding layer comprising p-InP to cover said Fe-doped InP current blocking regions and said second SCH InGaAsP layer, wherein said second cladding layer is covered with a contact layer of p-InGaAs; and j) forming a first electrical contact pad on said p-InGaAs contact layer in the area of said FP laser and a second electrical contact pad on said p-InGaAs contact layer in the area of said EA modulator.

12. The method as defined in claim 11, wherein the method further comprises the step of forming an isolation trench across the width of the device, through a predetermined depth of said second cladding layer and said contact layer in a region between the FP laser and the EA modulator.

13. The method as defined in claim 12 wherein the trench is formed using a reactive ion etching process.

14. The method as defined in claim 12 wherein the trench is formed to comprise a predetermined depth of approximately 0.7 microns and a width of approximately 20 microns.

15. The method as defined in claim 11, wherein a selective area growth process is used to perform step f).

16. The method as defined in claim 11, wherein the method further comprises the steps of:

a) forming a first reflective coating on a FP laser endface of the device; and b) forming a first anti-reflective coating on an EA modulator endface of the device.

17. A method for making a Fabry-Perot electroabsorption modulated laser, the method comprising the steps of:

a) providing an InP substrate including a top major surface;

b) covering said InP substrate top major surface with a masking layer;

c) etching a stripe in said masking layer to define the region wherein said laser will be formed;

d) depositing a first cladding layer comprising n-InP in the exposed stripe;

e) depositing a first separate confinement heterostructure (SCH) layer of InGaAsP to cover said first cladding layer;

f) forming a first MQW structure active region for a Fabry-Perot (FP) laser and a second MQW structure active region for an electroabsorption (EA) modulator on said first SCH layer, wherein said first MQW active region is optically coupled to said second MQW active region and said FP laser region exhibits thicker barrier and well layers than said BA modulator barrier and well layers;

g) depositing a second SCH InGaAsP layer to cover said MQW structures;

h) removing the remaining mask layer and growing Fe-doped InP current blocking regions on the exposed substrate surface to be coextensive with said second SCH InGaAsP layer;

i) depositing a second cladding layer comprising p-InP to cover said Fe-doped InP current blocking regions and said second SCH InGaAsP layer, wherein said second cladding layer is covered with a contact p-InGaAs layer;

j) forming a first electrical contact pad on said p-InGaAs contact layer in the area of said FP laser and a second electrical contact pad on said p-InGaAs contact layer in the area of said EA modulator; and k) forming a first reflective coating on a FP laser endface and a first anti-reflective coating on an EA modulator endface.

* * * * *